United States Patent [19]

Vasile et al.

[11] 4,248,092
[45] Feb. 3, 1981

[54] METHOD AND APPARATUS FOR EFFICIENTLY GENERATING ELASTIC WAVES WITH A TRANSDUCER

[75] Inventors: Carmine F. Vasile; Robert B. Thompson, both of Thousand Oaks, Calif.; Christopher M. Fortunko, Albuquerque, N. Mex.

[73] Assignee: Electric Power Research Institute, Inc., Palo Alto, Calif.

[21] Appl. No.: 32,993

[22] Filed: Apr. 25, 1979

Related U.S. Application Data

[63] Continuation-in-part of Ser. No. 916,445, Jun. 19, 1978, abandoned.

[51] Int. Cl.³ .............................................. G01N 29/04
[52] U.S. Cl. ................................................... 73/643
[58] Field of Search ........................... 73/643; 367/137

[56] References Cited

U.S. PATENT DOCUMENTS

| | | | |
|---|---|---|---|
| 3,786,672 | 1/1974 | Gaerttner | 73/643 |
| 3,850,028 | 11/1974 | Thompson et al. | 73/643 |
| 4,058,002 | 11/1977 | Moran | 73/643 |
| 4,127,035 | 11/1978 | Vasile | 73/643 |

Primary Examiner—Anthony V. Ciarlante
Attorney, Agent, or Firm—H. Fredrick Hamann; Craig O. Malin; John J. Deinken

[57] ABSTRACT

Disclosed is a method for generating an ultrasonic wave in a material, utilizing a transducer adapted to induce a higher than fundamental mode wave in the material and a signal generator adapted to drive the transducer at a frequency above the cutoff frequency below which the higher mode wave will not propagate. For a horizontal shear wave, optimal transducer efficiency is obtained by selecting a driven frequency between a minimum cutoff frequency $f_c = v_s n/2t$ and an upper frequency sufficiently close to $f_c$ to drive the transducer with at least a preselected increase in efficiency.

11 Claims, 7 Drawing Figures

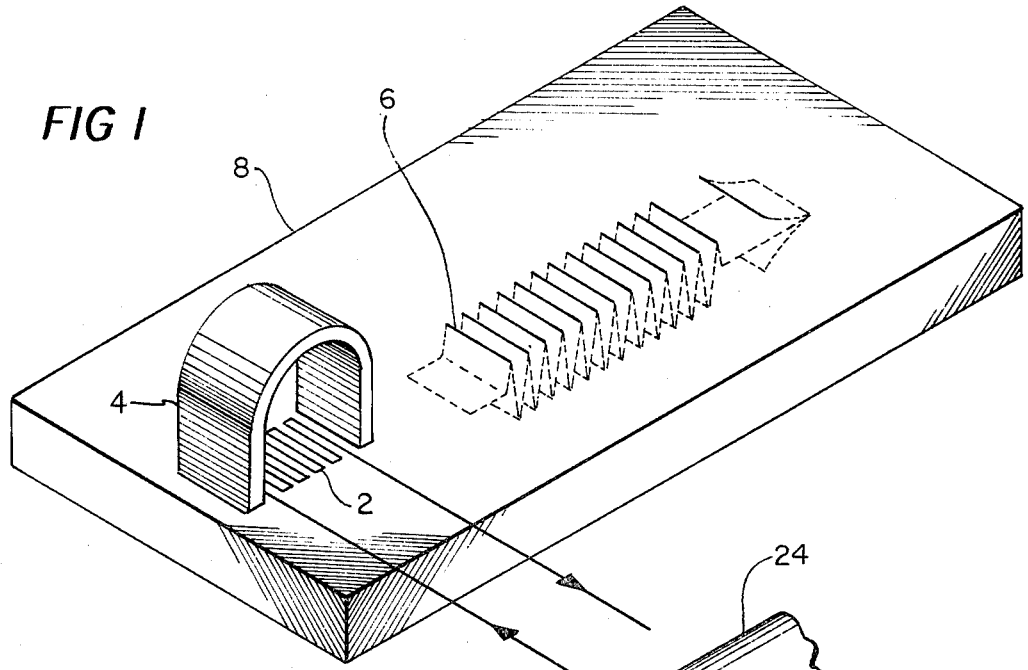
FIG 1
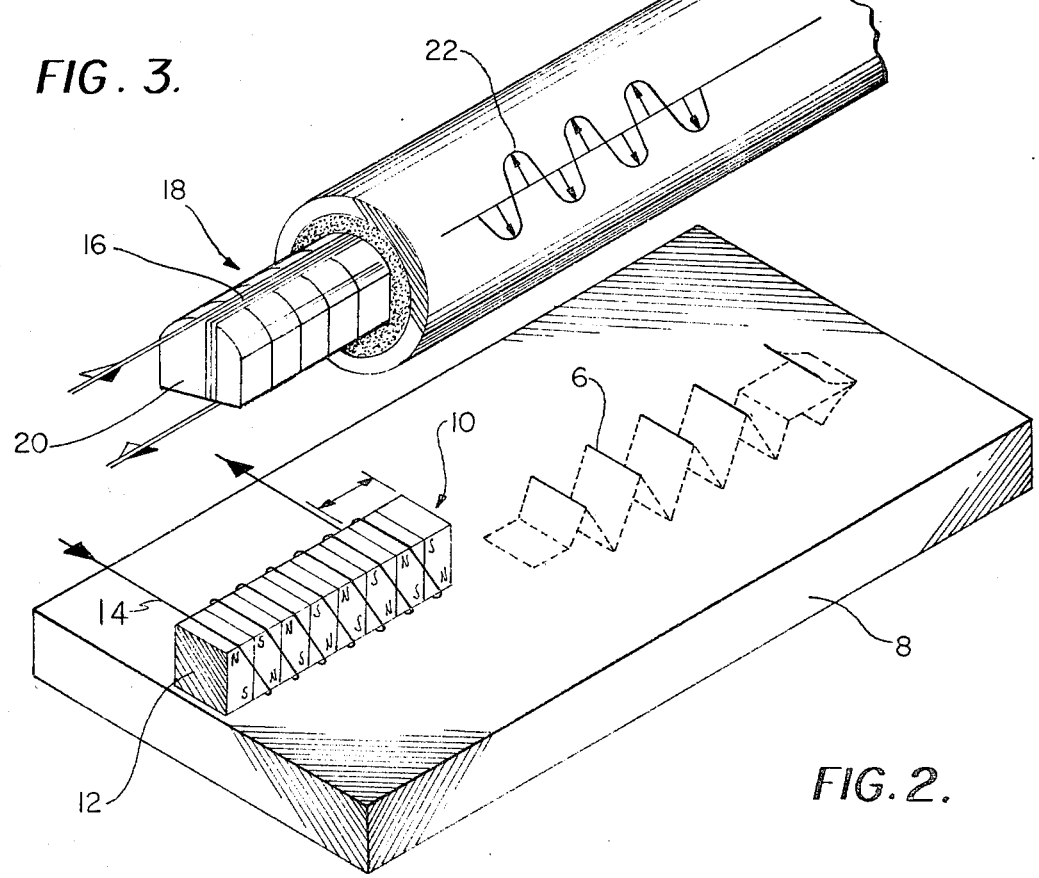
FIG. 3.
FIG. 2.

METHOD AND APPARATUS FOR EFFICIENTLY GENERATING ELASTIC WAVES WITH A TRANSDUCER

CROSS-REFERENCE TO RELATED APPLICATION

This application is a continuation-in-part of application Ser. No. 916,445, filed June 19, 1978 now abandoned.

BACKGROUND OF THE INVENTION

This invention relates to the field of inspection and particularly to the field of ultrasonic inspection of materials.

Conventional ultrasonic inspection techniques utilize a narrow beam of longitudinal or transverse type ultrasonic waves which is injected into the part being inspected by contacting the transducer with the part or by contacting the transducer with a transmitting medium, such as water, which also contacts the part. Such contact transducers generally employ piezoelectric crystals.

More recently, electromagnetic acoustic transducers (EMATs) have been developed which are capable of injecting ultrasonic waves into the part without any physical contact with the part. Because of the non-contact feature of such transducers, they are particularly useful in many nondestructive testing applications. One such electromagnetic transducer utilizes a periodic meander coil placed in a magnetic field. When an RF signal is applied to the meander coil, an ultrasonic wave is created in the test part, as described in U.S. Pat. No. 3,850,028.

A later developed type of electromagnetic acoustic transducer does not utilize a periodic meander coil. Rather, this type of transducer includes a row or stack of individual, alternately oriented permanent magnets which create a static, periodic magnetic field. One side of a coil is placed in the periodic magnetic field so that a sheet of current moves transverse to the magnetic field when a pulse of current flows through the coil. This latter type of transducer can be used to create horizontal shear (SH) waves and Lamb waves in an electrically conductive part, as described in U.S. Pat. No. 4,127,035.

The various EMATs described above are built with a particular periodicity D (determined by the spacing of a meander coil or of a row of magnets) which defines the wavelength, $\lambda$, of the ultrasonic wave which the EMAT is designed to generate. The frequency, f, used to generate the ultrasonic wave is then determined from the dispersion relationship between the wavelength, $\lambda$, and the velocity, v, of the wave in the particular material of the part being tested. The frequency of the fundamental horizontal shear wave mode, n=0, for example is given by the relationship $v = \lambda f$. The relationship is more complex for higher order modes and is based on dispersion curves characteristic of the mode type.

Unfortunately, however, electromagnetic transducers exhibit a low efficiency in operation as compared to piezoelectric transducers, which makes it difficult to use an EMAT to locate small defects. Consequently, methods and apparatus for increasing the operating efficiencies of electromagnetic transducers and other transducers which operate with reduced efficiency are needed in the art.

SUMMARY OF THE INVENTION

It is a general object of this invention to provide an improved method for generating ultrasonic waves.

A method for generating an ultrasonic wave in a material having a thickness t includes, according to the present invention, the steps of:

(a) positioning a transducer near a surface of the material, the transducer being selected to induce a higher than fundamental mode wave in the material, and (b) driving the transducer with an AC signal at a frequency which is selected to be above the minimum cutoff frequency for the higher mode wave but is sufficiently close to the cutoff frequency to drive the transducer with at least a preselected increase in efficiency relative to the efficiency attainable with a fundamental mode wave.

In more particular embodiments, the transducer may be configured to generate a higher mode Lamb wave or a higher mode horizontal shear wave. Where a horizontal shear wave is induced, the cutoff frequency $f_c$ is defined as:

$$f_c = v_s n / 2t$$

where $v_s$ = the velocity of the horizontal shear wave, n = the integral mode number of the horizontal shear wave.

The driven frequency may be selected according to the radiated power expression $$P_n \propto \frac{1}{\sqrt{1 - (\frac{n v_s}{2ft})^2}}$$

Examples of the more important features of this invention have thus been broadly outlined in order that the detailed description which follows may be better understood, and so that the contributions which this invention provides to the art may be better appreciated. There are, of course, additional features of the invention which will be described herein, and which are included wihin the subject matter of the claims appended hereto.

BRIEF DESCRIPTION OF THE DRAWINGS

Additional objects, features, and advantages of the present invention will become apparent by referring to the following detailed description of the preferred embodiments in connection with the accompanying drawings, wherein like reference numerals refer to like elements throughout all the FIGURES. In the drawings:

FIG. 1 is a perspective view of a meander coil transducer for generating Lamb waves in a plate;

FIG. 2 is a perspective view of a periodic magnet transducer with a transverse winding for generating Lamb waves in a plate;

FIG. 3 is a perspective view of a periodic magnet transducer with a longitudinal winding for generating horizontal shear waves (or torsional waves in a tube);

DESCRIPTION OF THE PREFERRED EMBODIMENT

Figure 4:
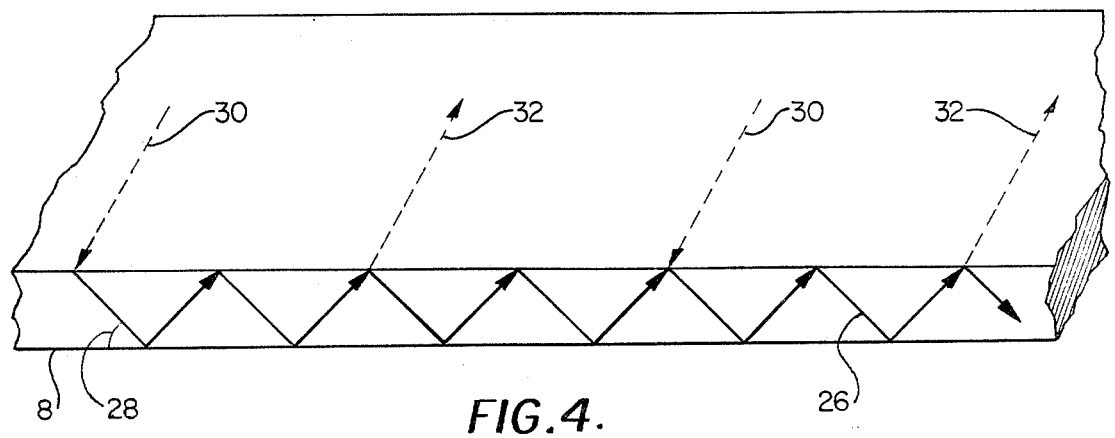
FIG. 4 is a schematic drawing illustrating the interaction between eddy currents and a multiply reflected shear wave in a plate.

FIGS. 1-3 show different types of electromagnetic acoustic transducers (EMATs) suitable for practicing the present invention. A meander coil 2, for example, when placed between the poles of a magnet 4, can be used to generate a Lamb wave 6 in a plate 8, as shown in FIG. 1. The wavelength, λ, of wave 6 is determined by the periodicity D of the meander coil 2.

Periodicity in the transducer can also be obtained by using a stack 10 of magnets 12, as shown in FIGS. 2 and 3. If a coil 14 is wrapped transversely to the stack 10, as illustrated in FIG. 2, then a Lamb wave 6 will be generated in the plate 8. If a coil 16 is wrapped longitudinally around a stack 18 of magnets, then a horizontal shear wave (a torsional wave in a tube) 22 is generated, as shown for the tube 24 in FIG. 3.

Other configurations and arrangements of electromagnetic transducers, as well as other types of transducers, can be utilized for practicing the invention, provided only that they are capable of inducing forces in the test part which will generate modes of vibration higher than the fundamental mode, generally n=1, 2, 3, 4, or 5.

Although noncontact transducers, such as the EMATs illustrated in FIGS. 1-3, are desirable for use in nondestructive testing applications, the low efficiency which has been demonstrated by such transducers relative to other transducers designs has heretofore been a disadvantage which has limited the useful applications of noncontact transducers. It is an outstanding feature of this invention, however, to provide an improved method by which the efficiency of operation of an ultrasonic transducer may be increased.

The principle on which the invention is based is illustrated in FIG. 4 in a perspective cross sectional view of a plate 8. A higher mode wave is shown as a reverberating shear wave 26 (the fundamental mode wave would propagate down the plate without reflecting from the plate boundaries). It consists of an initial shear wave which strikes the back surface of plate 8 at an incident angle 28 and is reflected at the same angle. The superposition of these two waves, and their subsequent reflections, become the higher mode shear wave 26, which propagates down the plate at an effective velocity slower than the velocity of the fundamental shear wave in the material, as a consequence of the greater distance traveled by the wave as it reflects from surface to surface.

Forces exerted in alternating directions in the material are created by eddy currents which are induced in the plate by the periodicity of an electromagnetic transducer, as shown by the lines 30, 32. When the transducer is operated near the minimum frequency (the cutoff frequency) at which the higher mode will propagate, a resonant condition is created due to the interaction between the forces 30, 32 and the higher mode wave. Consequently, a transducer of finite length will interact with the wave during a number of reflections and thereby may be used to build up a large amplitude ultrasonic wave. The higher mode wave generation will cease when the angle 28 reaches 90°, at which point the reverberating wave does not propagate down the plate and the frequency of operation corresponds to the cutoff frequency. This resonance effect is analogous to a similar effect known to occur with microwaves travelling in a waveguide.

Tests have been performed using a periodic magnet transducer, such as that shown in FIG. 3, to generate torsional waves in the 0.05 inch thick wall of a 0.875 inch diameter Inconel alloy tube. For the n=0 mode, (i.e. no reflections of the wave from the walls of the tube) the signal-to-noise ratio for direct transmission between two transducers was measured at 30 dB. When tests were run in the n=1 mode near the minimum cutoff frequency, the signal-to-noise ratio was found to increase to 56 dB. In addition to being excited with greater efficiency, the higher order mode was also found to be more sensitive to defects located near the tube surface, since most of the ultrasonic energy is concentrated in the near-surface region for higher mode waves.

Figure 5:
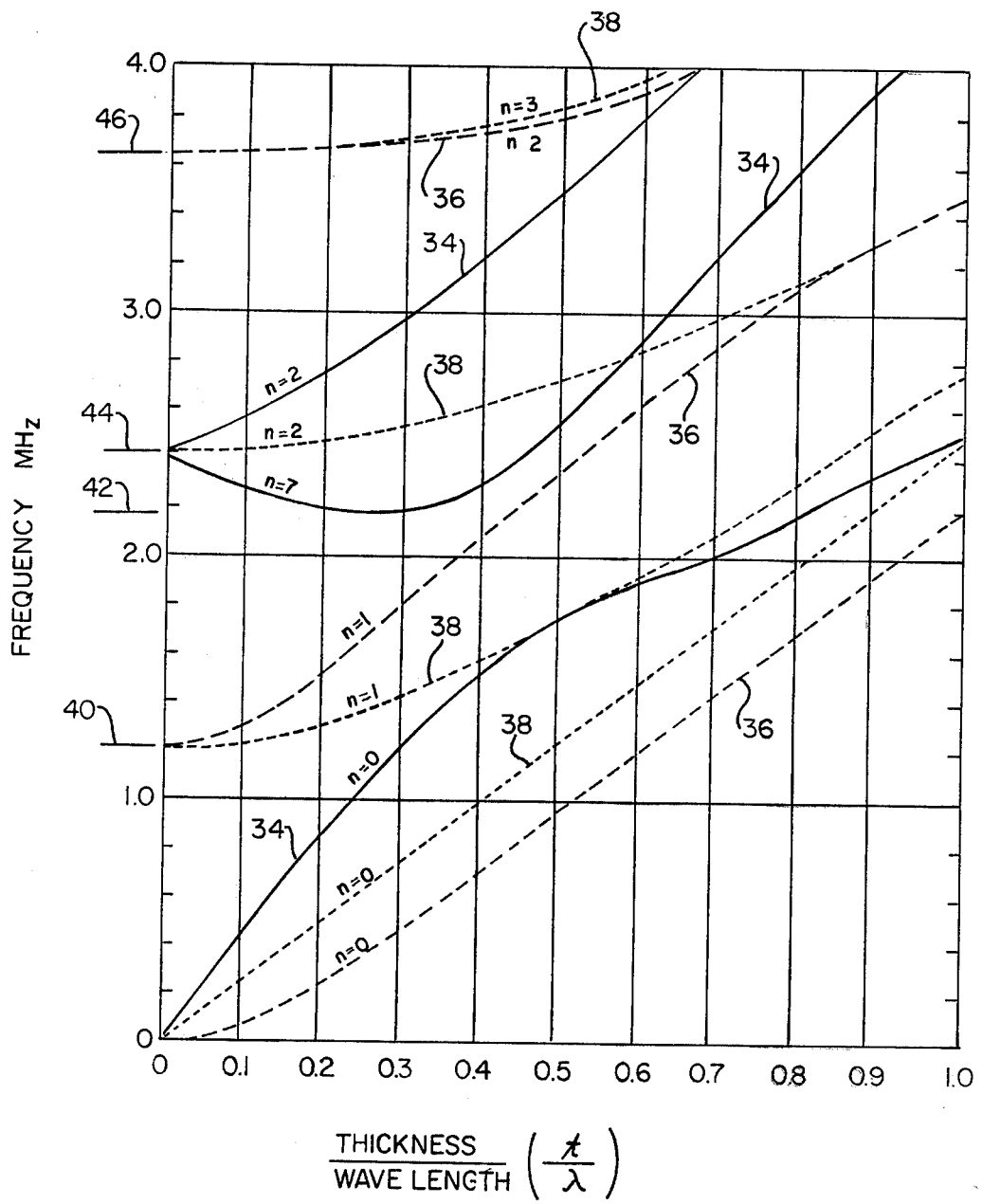
FIG. 5 depicts the relationship between frequency and wavelength in a 0.05 inch thick Inconel alloy plate for three modes of horizontal shear and Lamb waves.

FIG. 5 provides a graphic illustration of the dispersion curves in a 0.05 inch thick Inconel plate for the symmetric and antisymmetric Lamb waves, represented by curves 34 and 36 respectively, and the horizontally polarized shear (SH) wave represented by curves 38. The minimum cutoff frequency $f_c$ for a particular mode is the frequency at which the slope of the curve is zero, as shown at frequencies 40-46 for various higher order modes. For a horizontally polarized shear wave, the cutoff frequency $f_c$ can be calculated from the equation:

$$f_c = v_s n/2t, \tag{1}$$

where:

$v_s$ = the velocity of a shear wave in the material,
n = mode number ≧ 1, and
t = thickness of the part.

Again in the case of horizontal shear waves, the range of enhanced efficiency may be characterized by proceeding from the expression for the total power $P_n$ radiated by a transducer operating in a mode n:

$$P_n \propto \omega^2/Y_{2n} \tag{2}$$

where $$Y_{2n} = \rho \omega v_s \beta nt/\epsilon_n$$

is an admittance parameter defined as the ratio of power carried per unit r..m.s. of surface displacement, and $$\beta_n = \sqrt{k_s^2 - \left(\frac{n\pi}{t}\right)^2}$$

Substituting in (2) for $Y_{2n}$ and $\beta n$:

$$P_n \propto \frac{\omega}{\sqrt{k_s^2 - \left(\frac{n\pi}{t}\right)^2}} \tag{3}$$

Further substitution in (3) for $k_s$ elimination of constants yields:

$$P_n \propto \frac{1}{\sqrt{1 - \left(\frac{n\pi v_s}{\omega t}\right)^2}} \tag{4}$$

Relationship (4) indicates that the radiated power theoretically reaches a maximum at the cutoff frequency ($\omega_c = n\pi v_s/t$) and diminishes for frequencies higher than the cutoff frequency. Below the cutoff frequency, the expression is imaginary. Thus, the power expression confirms that a particular amount of enhanced transducer efficiency may be achieved by operating the transducer in a higher order mode at a frequency above the cutoff frequency for that mode but sufficiently close to the cutoff frequency to raise the efficiency to the desired level. For example, if twice the unenhanced efficiency is desired, the ratio $P_u/P_{\omega=\infty}$ is set equal to (2) and relationship (4) may be utilized to yield an upper frequency $f_u$ $$f_u = \frac{n V_s}{\sqrt{3} \, t}$$

or $$f_u = \frac{2 f_c}{\sqrt{3}} \approx 1.15 f_c$$

Thus, in order to achieve this particular efficiency enhancement, the transducer would be operated at a frequency between $f_c$ and 1.15 $f_c$.

The frequency $f_c$ and approximations for $f_u$ for Lamb wave modes and for the tube (torsional) modes obey similar, but mathematically more complex, relationships. For a particular type of wave, the frequency of the RF signal can be varied to generate higher order modes and the change in the amplitude or efficiency of wave generation may be measured as the frequency is varied. A rapid drop in amplitude indicates that the cutoff frequency has been reached.

The sensitivity of the efficiency/frequency relationship changes rapidly in the region very close to the cutoff frequency. Since the cutoff frequency varies inversely as the thickness of the material, normal variations in the material thickness can cause problems in the interpretation of data. However, such problems can be minimized if care is taken not to operate the transducer too close to the cutoff frequency, taking into consideration the variation in thickness of the material being inspected.

Figure 6:
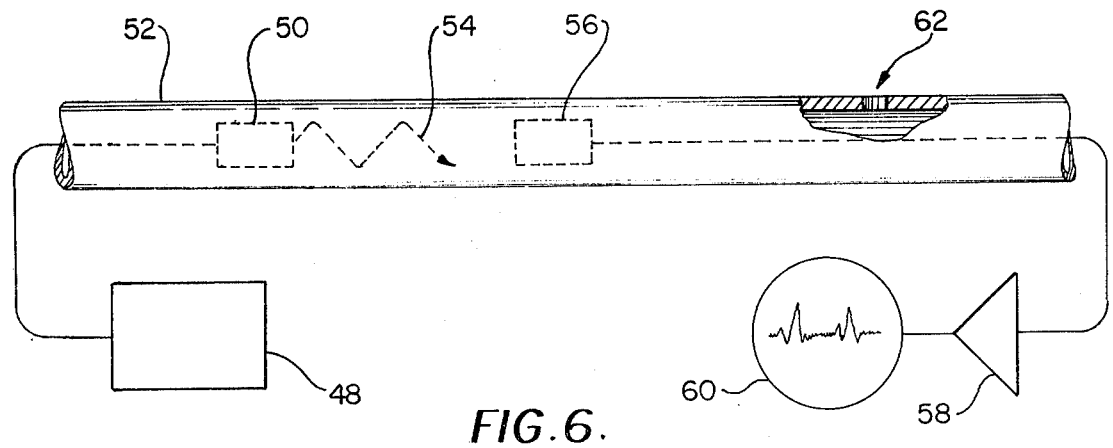
FIG. 6 is a schematic of a test apparatus for practicing the invention.

FIG. 6 is a schematic of a typical apparatus which may be used to practice the invention. A Matec RF pulse generator 48 supplies an AC signal at a selected frequency to the coil of an EMAT transmitter 50, which is placed in side a metal tube 52 being tested. This signal creates an acoustic wave 54, which travels in the tube 52 outward from the transmitter 50. An EMAT receiver 56 is placed in the tube to detect the acoustic wave 54 as it travels past receiver 56 and to detect the reflections or echoes of the wave 54 as they travel past the receiver 56. Receiver 56 may be similar in construction to transmitter 54, or a different type of EMAT can be used. The signal detected by the receiver 56 is amplified in a low noise amplifier 58 and displayed in an oscilloscope 60 or another suitable display device. For purposes of demonstration in a particular test which was conducted, a small hole 62 was drilled in the wall of the tube 52 to represent a defect in the test.

Figure 7:
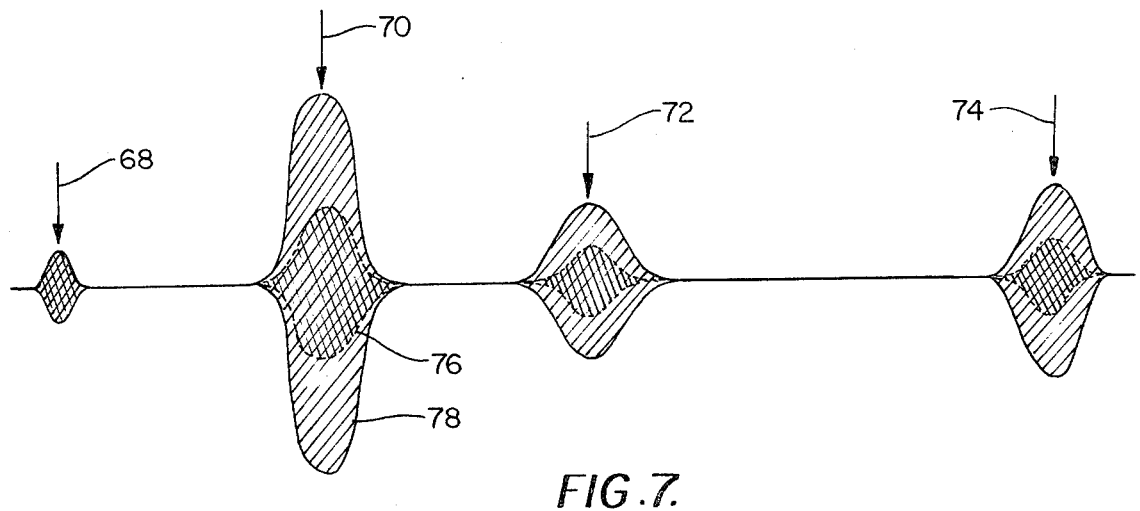
FIG. 7 shows the amplitude of a wave obtained utilizing the test apparatus of FIG. 6.

FIG. 7 shows typical ultrasonic wave forms which will be displayed by the oscilloscope 60 when the transmitter 50 is operated at two different frequencies in the arrangement shown in FIG. 6. The ultrasonic wave 54 was excited by an RF tone burst, and the 61 μsec width (at the −40 dB level) of the wave 54 transmitted directly between transmitter 50 and receiver 56 corresponded to a wave packet of spatial length equal to 7 inches along the tube. For this example, defects spaced closer than 3.5 inches along the tube axis would begin to overlap in time. Resolution of defects more closely spaced than 3.5 inches may be readily accomplished, however, by utilizing shorter transducers at the cost of lower sensitivity. The present invention provides for the recovery of the loss of efficiency which is suffered in the attempt to gain this increased sensitivity.

Since the higher order modes travel with a lower group velocity near the cutoff frequency, a second advantage is also realized with the present invention. For a given spatial resolution, a higher mode ultrasonic pulse will have a greater temporal duration than the fundamental mode. This means that the higher mode wave can be detected in a filter with a narrow bandwidth, thereby reducing noise and further improving sensitivity as compared to traditional techniques which operate with fundamental mode waves.

In FIG. 7, the first signal 68 represents the electrical feed-through which occurs when the transmitter electronics are activated. The next signal 70, at approximately 50 μsec, represents the ultrasonic wave which has propagated directly between transmitter 50 and receiver 56. In a system using a transmit-receive switch and a single transducer for both transmission and reception, this signal would occur at the same time as the feed-through signal 68 and hence would reduce the complexity of the display. Signal 72 illustrates the echo reflection from defect 62 and is of primary interest because it indicates the existence and location of the defect in the tube. Finally, signal 74 represents a reflection from the end of the tube.

The dashed trace 76 is typical in amplitude of signals obtained according to the prior art practice of selecting a frequency which will generate and receive the fundamental mode, n=0. It would also be typical for signals of higher order modes, n≧1, when the transmitter is not operated at frequencies sufficiently near the cutoff frequency $f_c$.

The solid trace 78 is typical of the amplitude of a signal obtained when a higher order mode is excited at a frequency near its cutoff, according to the present invention. For comparison, the peaks of the signals are shown as occurring at the same time although there normally would be a small horizontal shift between the two methods depending upon the frequencies used. Clearly, trace 78 provides a much higher signal-to-noise ratio than does trace 76. This improvement, which is obtained by utilizing the method of the present invention, increases the available sensitivity of ultrasonic inspection techniques utilizing electromagnetic acoustic transducers and enables the artisan to take advantage of the noncontact characteristics of EMATs in applications requiring a level of sensitivity which was not attainable utilizing previous inspection techniques.

Numerous variations and modifications may be made without departing from the present invention. Accordingly, it should be clearly understood that the form of the present invention described above and shown in the accompanying drawings is illustrative only and is not intended to limit the scope of the present invention.

What is claimed is:

1. A method for generating an ultrasonic wave in a material having a thickness t, comprising the steps of:
    positioning a transducer near a surface of the material, the transducer being selected to induce a higher than fundamental mode wave in the material; and driving the transducer with an AC signal at a frequency which is selected to be above the cutoff frequency for the higher mode wave but is sufficiently close to the cutoff frequency to drive the transducer with at least a preselected increase in efficiency relative to the efficiency attainable with a fundamental mode wave.

2. The method of claim 1, wherein the transducer is arranged to induce a horizontal shear wave, the cutoff frequency $f_c$ being defined as:

$$f_c = v_s n/2t$$

where $v_s$ = the velocity of the horizontal shear wave,
n = the integral mode number of the horizontal shear wave ($n \geq 1$).

3. The method of claim 2, wherein the driven frequency is selected to achieve the desired efficiency according to the radiated power expression $$P_n \propto \frac{1}{\sqrt{1 - (\frac{n v_s}{2 f t})^2}}$$

where:
$P_n$ = radiated power, and
f = frequency.

4. The method of claim 3, wherein the driven frequency is selected to be below an upper frequency $f_u$ defined as:

$$f_u = 1.15 f_c.$$

5. The method of claim 1, wherein the transducer is configured to generate a higher than fundamental mode Lamb wave.

6. An improved method for generating an ultrasonic wave in an electrically conductive material having a thickness t, the method including the steps of positioning an electromagnetic acoustic transducer near a surface of the material and driving the transducer with an AC signal at a frequency selected to generate an ultrasonic wave in the material, wherein the improvement comprises the steps of:
selecting a transducer adapted to induce a higher mode wave in the material; and
selecting a driving frequency which is above the cutoff frequency for the higher mode wave but is sufficiently close to the cutoff frequency to drive the transducer with at least a preselected increase in efficiency relative to the efficiency attainable with a fundamental mode wave.

7. The method of claim 6, wherein the higher mode wave induced is a horizontal shear wave and the cutoff frequency $f_c$ is defined as:

$$f_c = v_s n/2t$$

where:
$v_s$ = the velocity of the horizontal shear wave,
n = the integral mode number of the horizontal shear wave ($n \geq 1$).

8. The method of claim 6, wherein the transducer is configured to generate a higher than fundamental mode Lamb wave.

9. The method of claim 7, wherein the preselected increase in efficiency is compared to the fundamental mode wave efficiency according to the expression $$P_n \propto \frac{1}{\sqrt{1 - (\frac{n V_s}{2 f t})^2}}$$

where:
$P_n$ = radiated power.
f = frequency.

10. The method of claim 9, further comprising the step of limiting the driven frequency to no higher than an upper frequency $f_u$ equal to 1.15 times $f_c$.

11. A method for efficiently generating a horizontal shear wave in a material having a thickness t, comprising the steps of:
positioning a horizontal shear wave transducer near a surface of the material, the transducer being selected to induce a higher than fundamental mode wave in the material; and
driving the transducer with an AC signal at a frequency which is selected to be above the cutoff frequency for the higher mode wave but is sufficiently close to the cutoff frequency to drive the transducer with at least a preselected increase in efficiency relative to the efficiency attainable with a fundamental mode horizontal shear wave, the cutoff frequency $f_c$ being defined as:

$$f_c = v_s n/2t$$

where:
$v_s$ = the horizontal shear wave velocity in the material
n = the integral mode number of the wave ($n \geq 1$).

* * * * *